US012655456B2

(12) United States Patent
Kim et al.

(10) Patent No.: US 12,655,456 B2
(45) Date of Patent: Jun. 16, 2026

(54) DIMERIC STILBENE PRODUCTION METHOD USING CALLUS CULTURE MEDIUM OF PLANT

(71) Applicant: KOREA RESEARCH INSTITUTE OF BIOSCIENCE AND BIOTECHNOLOGY, Daejeon (KR)

(72) Inventors: Cha Young Kim, Daejeon (KR); Suhyun Park, Daejeon (KR); Yu Jeong Jeong, Daejeon (KR); Jae Cheol Jeong, Daejeon (KR); Young Bae Ryu, Daejeon (KR); Suk Weon Kim, Daejeon (KR); Jiyoung Lee, Daejeon (KR); Sung-Chul Park, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 0 days.

(21) Appl. No.: 18/480,868

(22) Filed: Oct. 4, 2023

(65) Prior Publication Data

US 2024/0026398 A1 Jan. 25, 2024

Related U.S. Application Data

(62) Division of application No. 17/293,172, filed as application No. PCT/KR2019/015487 on Nov. 13, 2019, now Pat. No. 11,814,661.

(30) Foreign Application Priority Data

Nov. 13, 2018 (KR) ........................ 10-2018-0139166
Nov. 13, 2019 (KR) ........................ 10-2019-0145478

(51) Int. Cl.
*C12P 17/04* (2006.01)
*A01H 4/00* (2006.01)

(52) U.S. Cl.
CPC ................ *C12P 17/04* (2013.01); *A01H 4/00* (2013.01)

(58) Field of Classification Search
CPC ..... C12N 5/00; C12N 5/04; C12P 7/22; C12P 17/04; A01H 4/00
See application file for complete search history.

(56) References Cited

FOREIGN PATENT DOCUMENTS

| | | | | |
|---|---|---|---|---|
| EP | 1519709 B1 | | 1/2004 | |
| EP | 2735609 A2 | * | 5/2014 | ........... C12N 5/0025 |
| KR | 10-2016-0001961 A | | 1/2016 | |
| KR | 10-2017-0106913 A | | 9/2017 | |
| WO | 2004006881 A2 | | 1/2004 | |

OTHER PUBLICATIONS

Wikipedia definition of centrifugation. https://en.wikipedia.org/wiki/Centrifugation. (Year: 2025).*

Sak et al. 2014. Elicitation of phenolic compounds in cell culture of Vitis vinifera L. by Phaeomoniella chlamydospora. Nova Biotechnologica et Chimica 13: 162-171. (Year: 2014).*

International Search Report dated Mar. 13, 2020 for International Patent Application No. PCT/KR2019/015487 (Authorized officer, Unknown), 4 pages with English translation.

Nopo-Olazabal et al., "Differential induction of antioxidant stilbenoids in hairy roots of Vitis rotundifolia treated with methyl jasmonate and hydrogen peroxide", Plant Physiology and Biochemistry, 2014, vol. 74, pp. 50-69.

Tisserant et al., "13C NMR and LC-MS Profiling of Stilbenes from Elicited Grapevine Hairy Root Cultures", Journal of Natural Products, 2016, vol. 79, No. 11, pp. 2846-2855.

Pezet et al., "δ-Viniferin, a Resveratrol Dehydrodimer: One of the Major Stilbenes Synthesized by Stressed Grapevine Leaves", Journal of Agricultural and Food Chemsitry, 2003, vol. 51, No. 18, pp. 5488-5492.

Keylor et al., "Chemistry and Biology of Resveratrol-Derived Natural Products", Chemical Reviews, 2015, vol. 115, pp. 8976-9027.

* cited by examiner

*Primary Examiner* — Karen M Redden
(74) *Attorney, Agent, or Firm* — MH2 Technology Law Group, LLP

(57) ABSTRACT

The present invention relates to a method for producing a dimeric stilbene using a plant callus culture solution. More specifically, the present invention relates to a method for producing a dimeric stilbene using a plant callus culture solution and a composition for dimeric stilbene production, which contains a plant callus culture solution as an active ingredient.

6 Claims, 5 Drawing Sheets

*trans*-Resveratrol *delta*-Viniferin

DIMERIC STILBENE PRODUCTION METHOD USING CALLUS CULTURE MEDIUM OF PLANT

CROSS-REFERENCE TO RELATED APPLICATIONS

This application is a divisional of U.S. application Ser. No. 17/293,172 filed 12 May 2021, which is a U.S. National Stage application of PCT/KR2019/015487 filed 13 Nov. 2019, which claims priority to Korean Application No. 10-2018-0139166 filed 13 Nov. 2018 and Korean Application No. 10-2019-0145478 filed 13 Nov. 2019, the entire disclosures of all of which are hereby incorporated by reference in their entireties.

TECHNICAL FIELD

The present invention relates to a method for producing a dimeric stilbene using a plant callus culture solution. More specifically, the present invention relates to a method for producing a dimeric stilbene using a plant callus culture solution and a composition for dimeric stilbene production, which contains a plant callus culture solution as an active ingredient.

BACKGROUND ART

Stilbenes, mainly expressed as resveratrol compounds, are a small class of plant secondary metabolites derived from the common phenylpropanoid pathway starting from phenylalanine. Resveratrol (3,4',5-transtrihydroxystilbene) is a naturally generated phytoalexin produced by some plants such as grapes, peanuts, and berries in response to environmental stresses such as UV irradiation or fungal infections. Resveratrol and its derivatives play an important role as phytoalexin and antioxidant in plant defense reactions as well as exhibit a variety of beneficial properties including anti-inflammatory effect, anti-tumor activity, and anti-aging effect. However, the potential use of trans-resveratrol is limited because of its instability in environments in which trans-resveratrol is exposed to light and oxygen or strong pH conditions.

Viniferin, one of the dimers of resveratrol, also exhibits various physiological activities such as anti-cancer, antiviral, anti-inflammatory, anti-aging, and antioxidant activities similar to resveratrol, and is thus used in functional health foods, cosmetics, pharmaceuticals, dyes, and functional livestock feed. In particular, viniferin is effective for liver protection, anti-cancer treatments, antioxidation, and skin whitening and is known to have the effect of inhibiting the oxidation of low-density lipoprotein and high-density lipoprotein and the proliferation and migration of vascular smooth muscle cells. More specifically, viniferin regulates tyrosinase, which changes tyrosine into melanocytes, and neutralizes cellular oxidation at the stage of dark spot formation, but the attack of free radicals stimulates tyrosinase. At this time, the powerful antioxidant activity of viniferin prevents the change of free radicals into melanocytes and thus provides clean and clear skin. Viniferin is also known to stop the circulatory response to oxidative stress and thus to prevent skin cell inflammation.

A method for extracting viniferin from grapevine sap is disclosed in European Patent No. EP1519709 as a method for producing viniferin with such high utilization. However, 1 ton of grapevine sap is required to extract 1 kg of viniferin.

Among the viniferins, delta-viniferin (δ-viniferin) is known to be obtained by bioconversion of trans-resveratrol using peroxidase (J. Agric. Food Chem. 2003, 51, 5488-5492). However, there is a disadvantage in that the price of peroxidase used at this time is high.

Hence, a method for efficiently producing viniferin in terms of cost and time is required.

The present invention has been made in view of the above requirement, and the present inventors have obtained a culture solution by suspension-culturing a plant callus, and have confirmed that a dimeric stilbene can be produced using the obtained culture solution. Accordingly, the present invention has been completed by revealing that it is possible to mass-produce a dimeric stilbene through the present invention, diminish the use of a solubilizing agent having a high unit price, and thus save the cost and time.

SUMMARY OF INVENTION

Technical Problem

An object of the present invention is to provide a method for producing a dimeric stilbene by bioconversion of a monomeric stilbene using a plant callus culture solution.

Another object of the present invention is to provide a method for producing a dimeric stilbene using a plant callus culture solution.

Still another object of the present invention is to provide a composition for dimeric stilbene production, which contains a plant callus culture solution as an active ingredient.

Solution to Problem

In order to achieve the above objects, the present invention provides a method for producing a dimeric stilbene using a plant callus culture solution, which includes:

1) suspension-culturing a plant callus in a culture medium and collecting the culture solution; and
2) adding a monomeric stilbene and an oxidizing agent to the culture solution collected in step 1) and stirring the mixture.

The present invention also provides a composition for dimeric stilbene production, which contains a plant callus culture solution and an oxidizing agent as active ingredients.

The present invention also provides a method for producing maackin as a dimeric stilbene using a plant callus culture solution, which includes adding an extraction solvent to a grape callus culture solution as a plant callus culture solution and extracting maackin as a dimeric stilbene.

The present invention also provides a composition for production of maackin as a dimeric stilbene, which contains a grape callus culture solution as a plant callus culture solution as an active ingredient.

Advantageous Effects of Invention

In the present invention, a culture solution has been obtained by suspension-culturing a plant callus, and it has been confirmed that a dimeric stilbene, more specifically, δ-viniferin, piceatannol dimer, and maackin can be produced using the obtained culture solution. Consequently, the method according to the present invention can be usefully used as a method for producing a dimeric stilbene.

In addition, the method according to the present invention has an advantage of saving the cost and time since the use of a solubilizing agent having a high unit price can be diminished in the method. In addition, since only the culture solution is recovered and used for the reaction, the callus that is not used for the reaction can be continuously used by being recovered and succeeded for the next culture, and the time and cost for the reaction can be saved.

DESCRIPTION OF EMBODIMENTS

Figure 1:
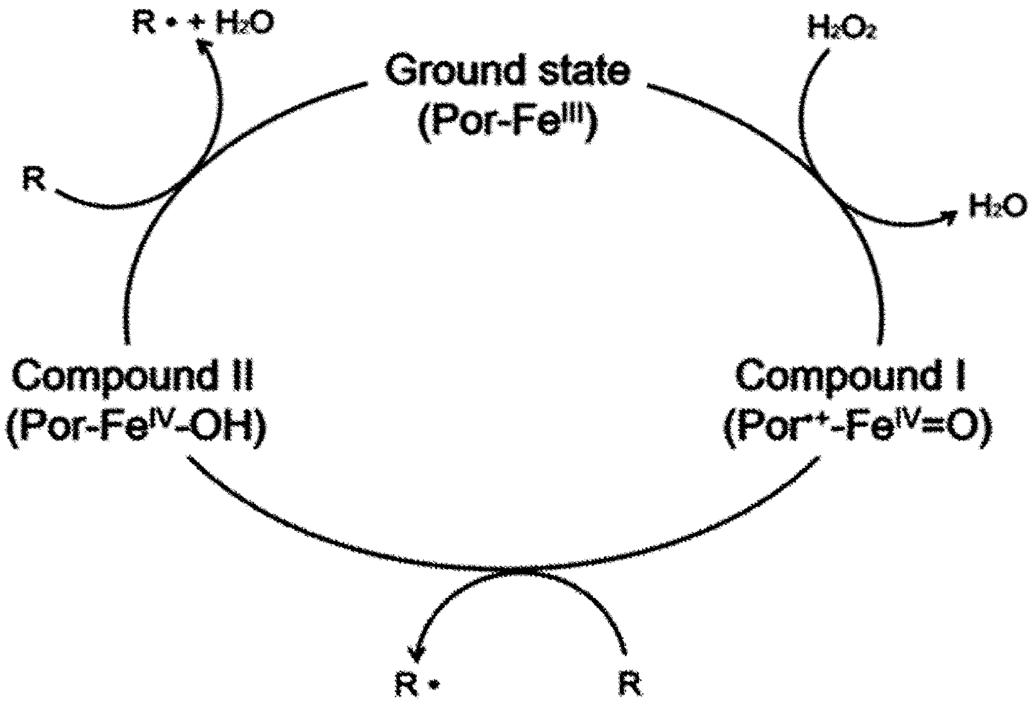
FIG. 1 illustrates a catalytic process in which peroxidase dehydrogenates a substrate using hydrogen peroxide as an oxidizing agent.
Figure 2:
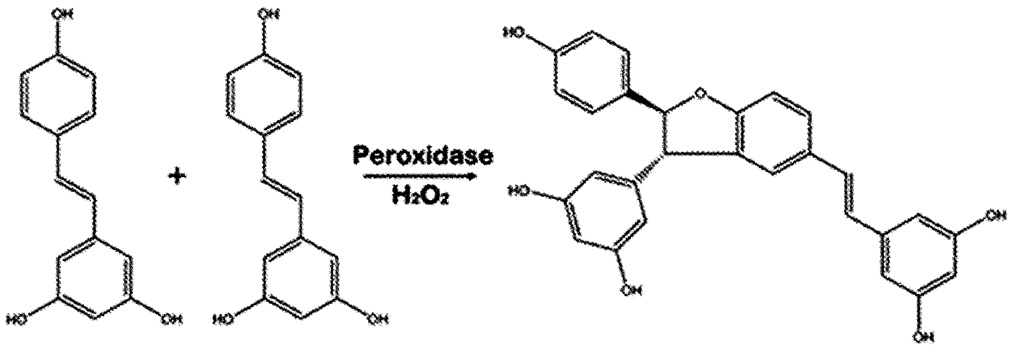
FIG. 2 illustrates the process of bioconversion of two monomeric resveratrols into δ-viniferin as a resveratrol dimer by peroxidase.

Hereinafter, the present invention will be described in more detail.

The present invention provides a method for producing a dimeric stilbene using a plant callus culture solution, which includes:

1) suspension-culturing a plant callus in a culture medium and collecting the culture solution; and
2) adding a monomeric stilbene and an oxidizing agent to the culture solution collected in step 1) and stirring the mixture.

In the method according to the present invention, the plant in step 1) may be shrubby sophora, grape, chokeberry, or soybean, but is not limited thereto.

In the method according to the present invention, the plant callus in step 1) may be obtained by placing a plant tissue section on a callus-inducing medium and inducing a plant tissue callus, or those distributed from the depository institution may be used.

The callus-inducing medium may be a medium to which 0.05 to 0.2 mg/L IAA (indole-3-acetic acid), 0.05 to 0.2 mg/L NAA (1-naphthaleneacetic acid), 1 to 2 mg/L 2,4-D (2-4-dichlorophenoxy acetic acid), and 0.2 to 0.3 mg/L kinetin as growth regulators are added. More specifically, the callus-inducing medium may be a medium to which 0.1 mg/L IAA (indole-3-acetic acid), 0.1 mg/L NAA (1-naphthaleneacetic acid), 1.5 mg/L 2,4-D (2-4-dichlorophenoxy acetic acid), and 0.25 mg/L kinetin are added, but is not limited thereto.

In the method according to the present invention, the culture medium in step 1) may be MS (Murashige & Skoog) medium containing 0.5 to 2.0 mg/L 2,4-D, more specifically MS (Murashige & Skoog) medium containing 1 mg/L 2,4-D, but is not limited thereto.

In the method according to the present invention, suspension culture in step 1) may be performed for 2 to 6 days, more specifically for 3 to 5 days, still more specifically for 4 days, but is not limited thereto.

In the method according to the present invention, the monomeric stilbene in step 2) may be resveratrol or piceatannol.

In the method according to the present invention, the oxidizing agent in step 2) is used in the dehydrogenation reaction for bioconversion of a monomeric stilbene into a dimeric stilbene, and may be, more specifically, hydrogen peroxide, but is not limited thereto.

In the method according to the present invention, stirring in step 2) may be performed for 3 to 7 minutes, more specifically for 4 to 6 minutes, still more specifically for 5 minutes, but is not limited thereto.

In the method according to the present invention, a step of adding an extraction solvent to the culture solution stirred in step 2) and extracting a dimeric stilbene may be further included. Here, the extraction solvent may be ethyl acetate, but is not limited thereto.

In the method according to the present invention, the dimeric stilbene may be δ-viniferin or piceatannol dimer.

In the method according to the present invention, the following step 3) may be further included after step 2):

3) additionally reacting the culture solution stirred in step 2) for 5 to 20 minutes, more specifically, for 7 to 20 minutes, still more specifically 10 to 20 minutes to obtain a crystal.

Through the reaction in step 3), a bioconverted dimeric stilbene that exhibits a property of being poorly soluble in water is precipitated as a crystal.

In the method according to the present invention, a step of adding an extraction solvent to the crystal obtained in step 3) and extracting a dimeric stilbene may be further included. Here, the extraction solvent may be methanol or an aqueous methanol solution, more specifically an aqueous methanol solution, but is not limited thereto. The dimeric stilbene may be δ-viniferin.

In a specific embodiment of the present invention, the present inventors have suspension-cultured shrubby sophora, grape, chokeberry, or soybean callus as a plant callus and collected the culture solution according to the present invention. Next, resveratrol as a monomeric stilbene and hydrogen peroxide as an oxidizing agent have been added to the collected culture solution and the mixture has been stirred for bioconversion of resveratrol, whereby it has been confirmed that δ-viniferin as a dimeric stilbene can be produced.

In addition, resveratrol as a monomeric stilbene and hydrogen peroxide as an oxidizing agent have been added to the collected culture solution, and the mixture has been stirred for bioconversion of resveratrol and then additionally reacted for 10 minutes or more to obtain a crystal. The crystal has been extracted and analyzed, and, as a result, δ-viniferin has been confirmed in the crystal.

The present inventors have suspension-cultured grape callus as a plant callus and collected the culture solution according to the present invention. Next, piceatannol as a monomeric stilbene and hydrogen peroxide as an oxidizing agent have been added to the collected culture solution and the mixture has been stirred for bioconversion of piceatannol, whereby it has been confirmed that piceatannol dimer as a dimeric stilbene can be produced.

Thus, in the present invention, it has been confirmed that a dimeric stilbene can be produced by suspension-culturing a plant callus, recovering the culture solution, and bioconverting a monomeric stilbene using hydrogen peroxide as an oxidizing agent together with the recovered culture solution.

It has been confirmed that crystals can be obtained by additionally reacting the culture solution subjected to bioconversion and a dimeric stilbene can be extracted from the obtained crystals.

Accordingly, the method according to the present invention can be usefully used as a method for producing a dimeric stilbene. In addition, the method according to the present invention has an advantage of saving the cost and time since the use of a solubilizing agent a high unit price can be diminished in the method. In addition, since only the culture solution is recovered and used for the reaction, the callus that is not used for the reaction can be continuously used by being recovered and succeeded for the next culture, and the time and cost for the reaction can be diminished.

The present invention also provides a composition for dimeric stilbene production, which contains a plant callus culture solution and an oxidizing agent as active ingredients.

In the present invention, the plant may be shrubby sophora, grape, chokeberry, or soybean, but is not limited thereto.

In the present invention, the plant callus may be obtained by placing a plant tissue section on a callus-inducing medium and inducing a plant tissue callus, or those distributed from the depository institution may be used.

In the present invention, the culture solution may be obtained by suspension-culturing a plant callus for 2 to 6 days, more specifically for 3 to 5 days, still more specifically for 4 days in a culture medium and collecting the culture solution, but is not limited thereto.

In the present invention, the oxidizing agent is used in the dehydrogenation reaction for bioconversion of a monomeric stilbene into a dimeric stilbene, and may be, more specifically, hydrogen peroxide, but is not limited thereto.

In the present invention, the dimeric stilbene may be δ-viniferin or piceatannol dimer, but is not limited thereto.

The present inventors have suspension-cultured a plant callus and recovered the culture solution, and have confirmed that a dimeric stilbene can be produced by bioconverting a monomeric stilbene using hydrogen peroxide as an oxidizing agent together with the recovered culture solution. Accordingly, the plant callus culture solution and an oxidizing agent can be usefully used as active ingredients of a composition for dimeric stilbene production.

The present invention also provides a method for producing maackin as a dimeric stilbene using a plant callus culture solution, which includes adding an extraction solvent to a grape callus culture solution as a plant callus culture solution and extracting maackin as a dimeric stilbene.

The present invention also provides a composition for production of maackin as a dimeric stilbene, which contains a grape callus culture solution as a plant callus culture solution as an active ingredient.

In the present invention, the grape callus may be obtained by placing grape tissue section on a callus-inducing medium and inducing grape tissue callus, or those distributed from the depository institution may be used.

In the present invention, the culture solution may be obtained by suspension-culturing grape callus for 2 to 6 days, more specifically for 3 to 5 days, still more specifically for 4 days in a culture medium and collecting the culture solution, but is not limited thereto.

In the present invention, the culture medium may be MS (Murashige & Skoog) medium containing 0.5 to 2.0 mg/L 2,4-D, more specifically MS (Murashige & Skoog) medium containing 1 mg/L 2,4-D, but is not limited thereto.

In the present invention, an extraction solvent may be added to the culture solution to extract maackin, and the extraction solvent may be ethyl acetate, but is not limited thereto.

In the present invention, maackin is represented by the following Chemical Formula (1).

[Chem. 1]

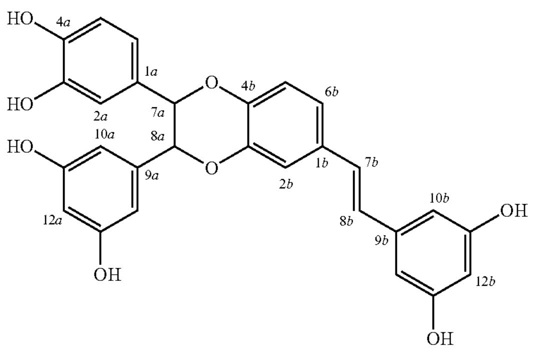

In a specific embodiment of the present invention, the present inventors have suspension-cultured grape callus and collected the culture solution according to the present invention. Next, the collected culture solution has been extracted with an extraction solvent, whereby it has been confirmed that maackin as a dimeric stilbene can be produced. Accordingly, the grape callus culture solution can be usefully used as an active ingredient in a method for producing maackin as a dimeric stilbene and a composition for maackin production.

EXAMPLES

Hereinafter, the present invention will be described in detail with reference to Examples.

However, the following Examples are only illustrative of the present invention, and the contents of the present invention are not limited to the following Examples.

<Example 1> Suspension Culture of Shrubby Sophora Callus and Recovery of Culture Solution for Bioconversion In the present invention, shrubby sophora callus was used for bioconversion. As for the shrubby sophora callus, shrubby sophora callus (BP1429378) distributed from KCTC (Korean Collection for Type Cultures) was used.

The shrubby sophora callus that had been distributed and stabilized was suspension-cultured. At the time of suspension culture, MS1D (MS 4.4 g, sucrose 30 g, MES (2-(N-morpholino)ethanesulfonic acid) 0.5 g, myo-inositol 0.1 g, thiamine-HCl 0.4 mg, 2,4-D 1 mg/L) liquid medium referring to MS (Murashige & Skoog) medium containing 1 mg/L 2,4-D (2-4-dichlorophenoxy acetic acid) was used. Into a 125 mL Erlenmeyer flask containing 20 mL of MS1D medium, 2 g of shrubby sophora callus was inoculated, and it was suspension cultured at 25° C. and 90 rpm for 4 days in dark conditions. On the fourth day of culture, the sample was filtered through a sieve to separate the callus and the callus culture solution from each other. The first separated culture solution sample was centrifuged at 3,000 rpm for 2 minutes to completely separate the callus and the culture solution from each other, and this culture solution was used in the bioconversion experiment.

<Example 2> Bioconversion of Resveratrol Using Shrubby Sophora Callus Culture Solution The shrubby sophora callus culture solution prepared in <Example 1>, 1 mM hydrogen peroxide, and 1 mM resveratrol as a monomeric stilbene were added into a 2 mL e-tube, and the mixture was stirred for 5 minutes in a rotary shaker to induce the dimerization reaction of resveratrol.

As a control, MS1D medium containing the same amount of HRP (Horseradish peroxidase) as the quantitative value of total proteins present in the shrubby sophora callus culture solution, 1 mM hydrogen peroxide, and 1 mM resveratrol were added into an e-tube, and the mixture was stirred for 5 minutes in a rotary shaker to induce the bioconversion of resveratrol. As a negative control, a sample in which only resveratrol and hydrogen peroxide were mixed with MS1D medium was used.

Figure 3:
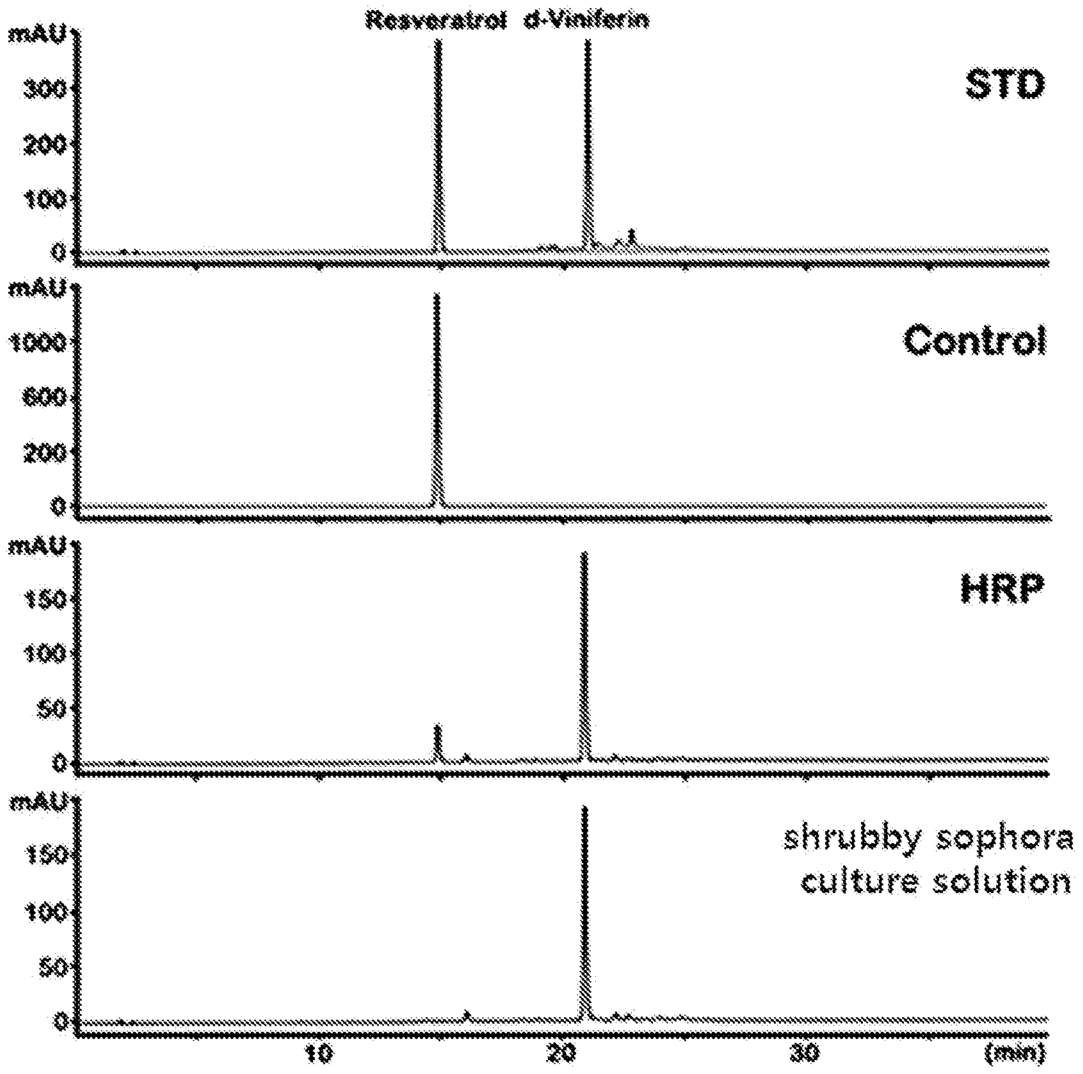
FIG. 3 illustrates the HPLC analysis results for a product obtained by bioconversion of resveratrol using a shrubby sophora callus culture solution as a plant callus culture solution according to the present invention.

<Example 3> Delta-Viniferin (δ-Viniferin) Extraction from Culture Solution Subjected to Bioconversion and HPLC Analysis Each sample reacted in <Example 2> was subjected to water-ethyl acetate partition and extraction with the same amount of ethyl acetate. Air was injected into the obtained ethyl acetate layer for drying, and the dried product was dissolved in 400 μl of 80% methanol, filtered through a 0.2 μm PTFE filter (hydrophilic, ADVANTEC, Japan), and then used in HPLC analysis. HPLC analysis was performed using the Agilent Technology 1200 series. A quaternary pump was used as the pump system, and Agilent ZORBAX SB-18 (5 mm, 4.6×150 mm) was used as the column. The analysis was performed using gradient elution using water (A, 0.05% trifluoroacetic acid) and acetonitrile (B, 0.05% trifluoroacetic acid) as the mobile phase. Stilbene compounds were confirmed at a wavelength of 300 nm using DAD (Diode Array Detector). In the negative control, δ-viniferin that was a dimeric stilbene of monomeric resveratrol was not observed at all. However, in the extract of a sample to which the shrubby sophora callus culture solution or HRP was added, a similar level of δ-viniferin was detected (FIG. 3). The cost of the medium (0.9 mL) used in <Example 2> is 5.2 won, the cost (23,212 won) of HRP (12.48 mg) that is in the same amount as the total proteins contained in the shrubby sophora callus culture solution is added to the cost of the medium, and it can be thus seen that it is significantly advantageous to use a shrubby sophora callus culture solution to produce the same amount of δ-viniferin.

<Example 4> Suspension Culture of Several Plant Calluses and Recovery of Culture Solution In order to confirm bioconversion using plant callus culture solutions other than a shrubby sophora callus culture solution, chokeberry callus, soybean callus, and grape (*Vitis vinifera* L. cv Campbell Early) callus were used. Each of the calluses was distributed from KCTC and used by the same method as the method described in <Example 1>. Next, 2 g of each of the chokeberry callus, soybean callus, and grape callus was inoculated into 20 mL MS1D liquid medium and then suspension culture and centrifugation were performed by the same method as the method described in <Example 1> to obtain each callus culture solution, and these callus culture solutions were used in the bioconversion experiment.

Figure 4:
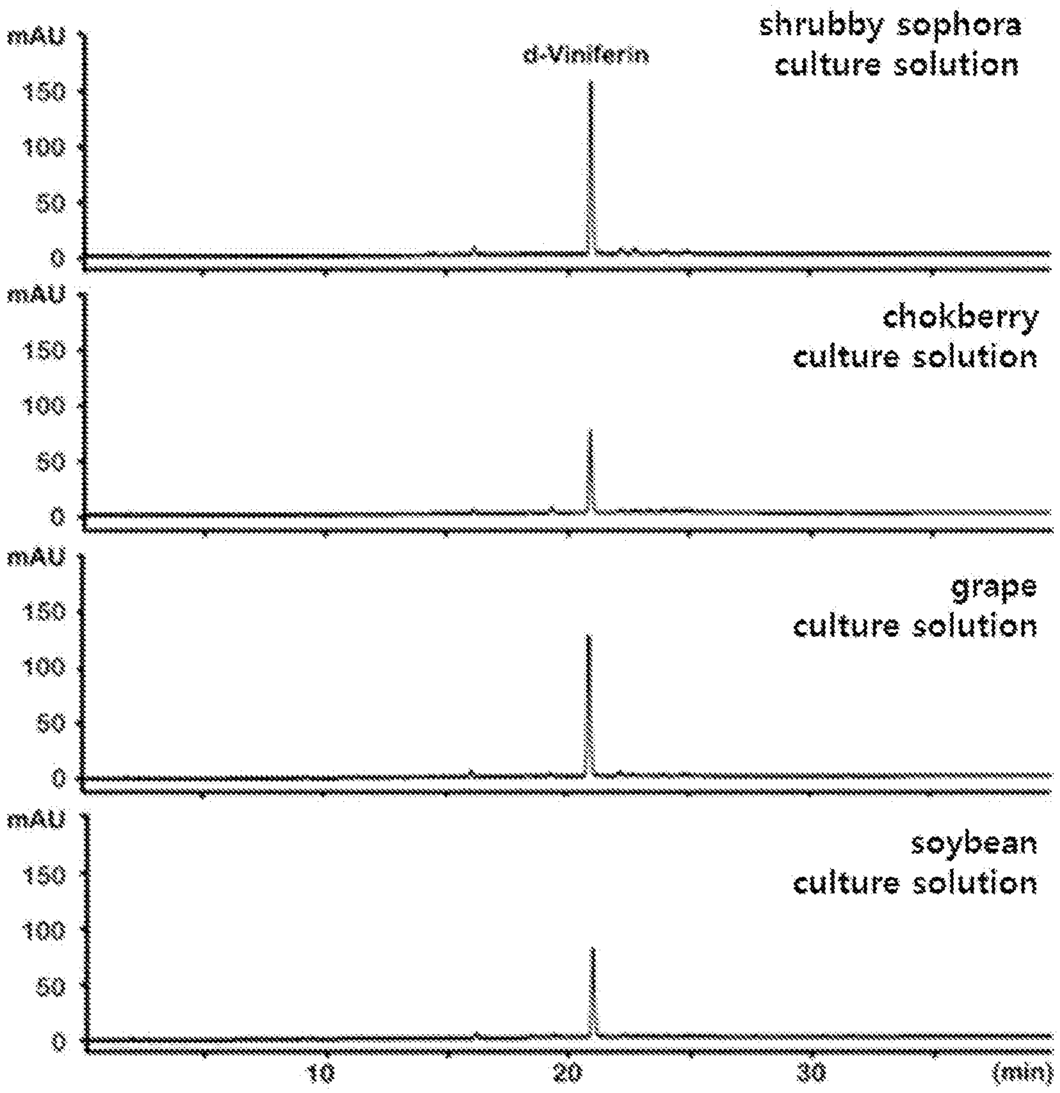
FIG. 4 illustrates the HPLC analysis results for products obtained by bioconversion of resveratrol using shrubby sophora, chokeberry, and grape callus culture solutions as a plant callus culture solution according to the present invention.

<Example 5> Bioconversion of Resveratrol Using Various Plant Callus Culture Solutions Each of the chokeberry callus culture solution, soybean callus culture solution, and grape callus culture solution prepared in <Example 4>, 1 mM hydrogen peroxide, and 1 mM resveratrol were added into a 2 mL e-tube, and the mixture was stirred for 5 minutes in a rotary shaker to induce the bioconversion of resveratrol. Next, each of the culture solutions subjected to the induction of bioconversion was extracted and then subjected to HPLC analysis by the same method as the method described in <Example 3> to confirm the production of a resveratrol dimer. As a result, it was confirmed that δ-viniferin was detected in the chokeberry callus culture solution, soybean callus culture solution, and grape callus culture solution subjected to the induction of bioconversion although the efficiency was different depending on the kind of plant (FIG. 4).

Figure 5:
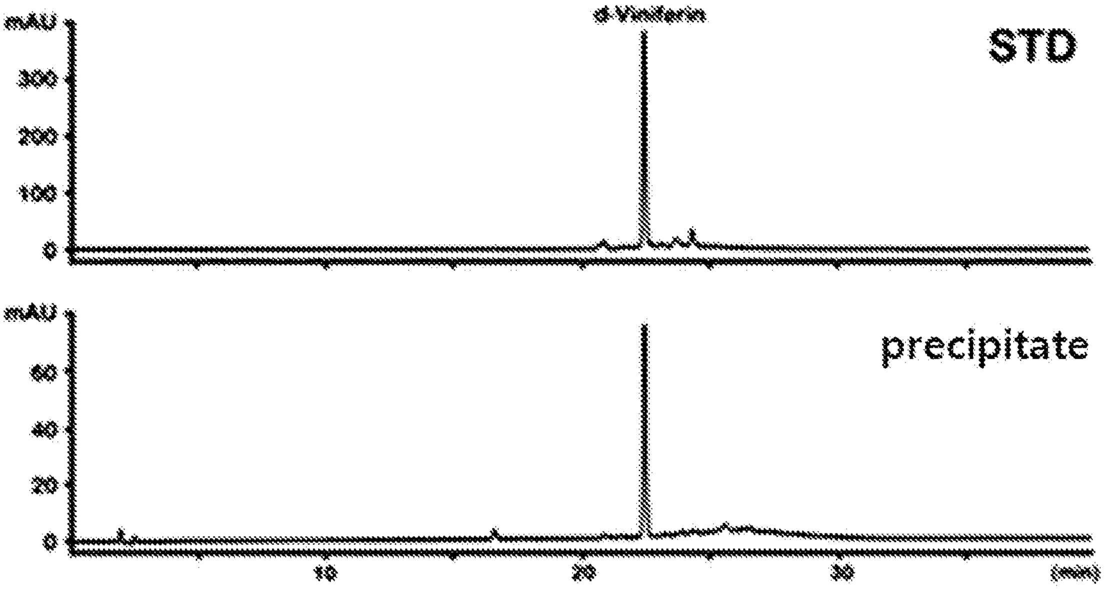
FIG. 5 illustrates the HPLC analysis results for a crystal obtained by bioconversion of resveratrol using a shrubby sophora callus culture solution as a plant callus culture solution according to the present invention and an additional reaction.

<Example 6> Delta-Viniferin Extraction from Reaction Products of Various Plant Callus Culture Solutions and HPLC Analysis The shrubby sophora callus culture solution recovered in <Example 2> was subjected to bioconversion by the same method as the method described in <Example 3> and then an additional reaction for 10 minutes or more was conducted, and as a result, it was confirmed that yellow crystals were precipitated. The culture solution containing the crystals was centrifuged at 12,000 rpm for 10 minutes to separate the pellet and the supernatant from each other, the supernatant was removed, and then air was injected into the obtained pellet for drying. The dried product was dissolved in 80% methanol at a concentration of 1 mg/ml, filtered through a 0.2 μm PTFE filter (hydrophilic, ADVANTEC, Japan), and subjected to HPLC analysis. As a result, 75% of the precipitated substances was identified as δ-viniferin. It can be seen that the extraction steps for obtaining the product can be decreased in the case of using the precipitation method described above as compared to the case of using an existing method (FIG. 5).

Each of the chokeberry callus culture solution, soybean callus culture solution, and grape callus culture solution prepared in <Example 4> was subjected to bioconversion by the same method as the method described in <Example 5> and then an additional reaction for 10 minutes or more was conducted. As a result, it was confirmed that yellow crystals were precipitated. Each of the culture solutions containing the crystals was also subjected to HPLC analysis as described above, and as a result, δ-viniferin was confirmed in the precipitated substances (analysis results are not included).

Figure 6:
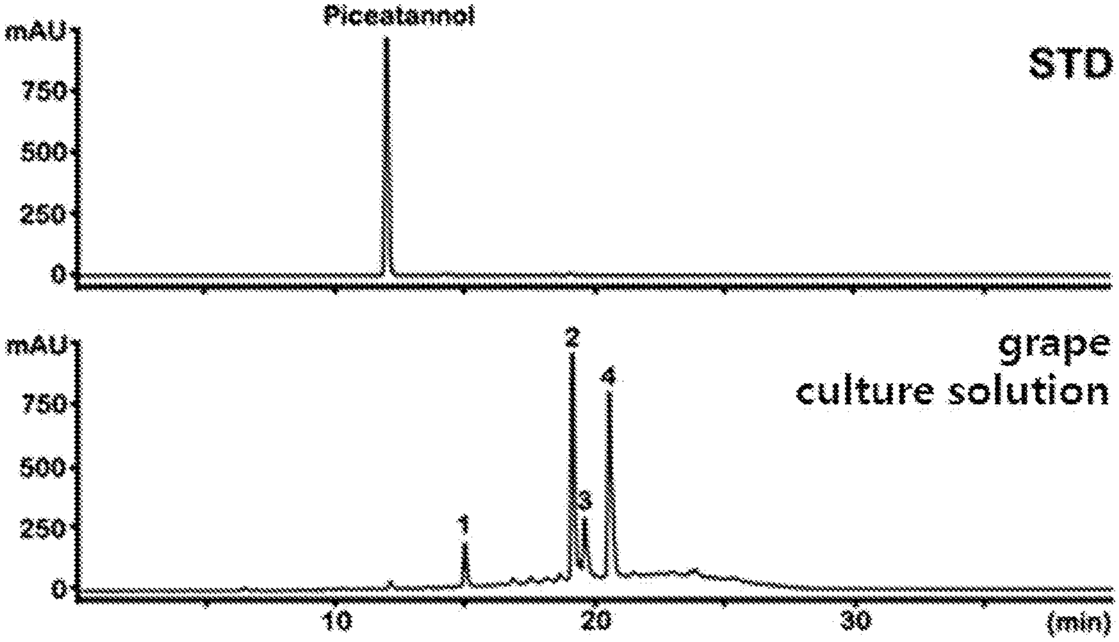
FIG. 6 illustrates the HPLC analysis results for a product obtained by bioconversion of monomeric piceatannol using a grape callus culture solution as a plant callus culture solution according to the present invention.

<Example 7> Bioconversion of Piceatannol Using Grape Callus Culture Solution The grape callus culture solution prepared in <Example 4>, 2 mM hydrogen peroxide, and 1 mM piceatannol as a monomeric stilbene were added into a 2 mL e-tube, and the mixture was stirred for 5 minutes in a rotary shaker to induce the bioconversion of piceatannol. Next, the culture solution subjected to the induction of bioconversion was extracted and then subjected to HPLC analysis by the same method as the method described in <Example 3> to confirm the production of a piceatannol dimer. As a result, four new peaks were confirmed in addition to the peak attributed to piceatannol added as a substrate (FIG. 6).

Figure 7:
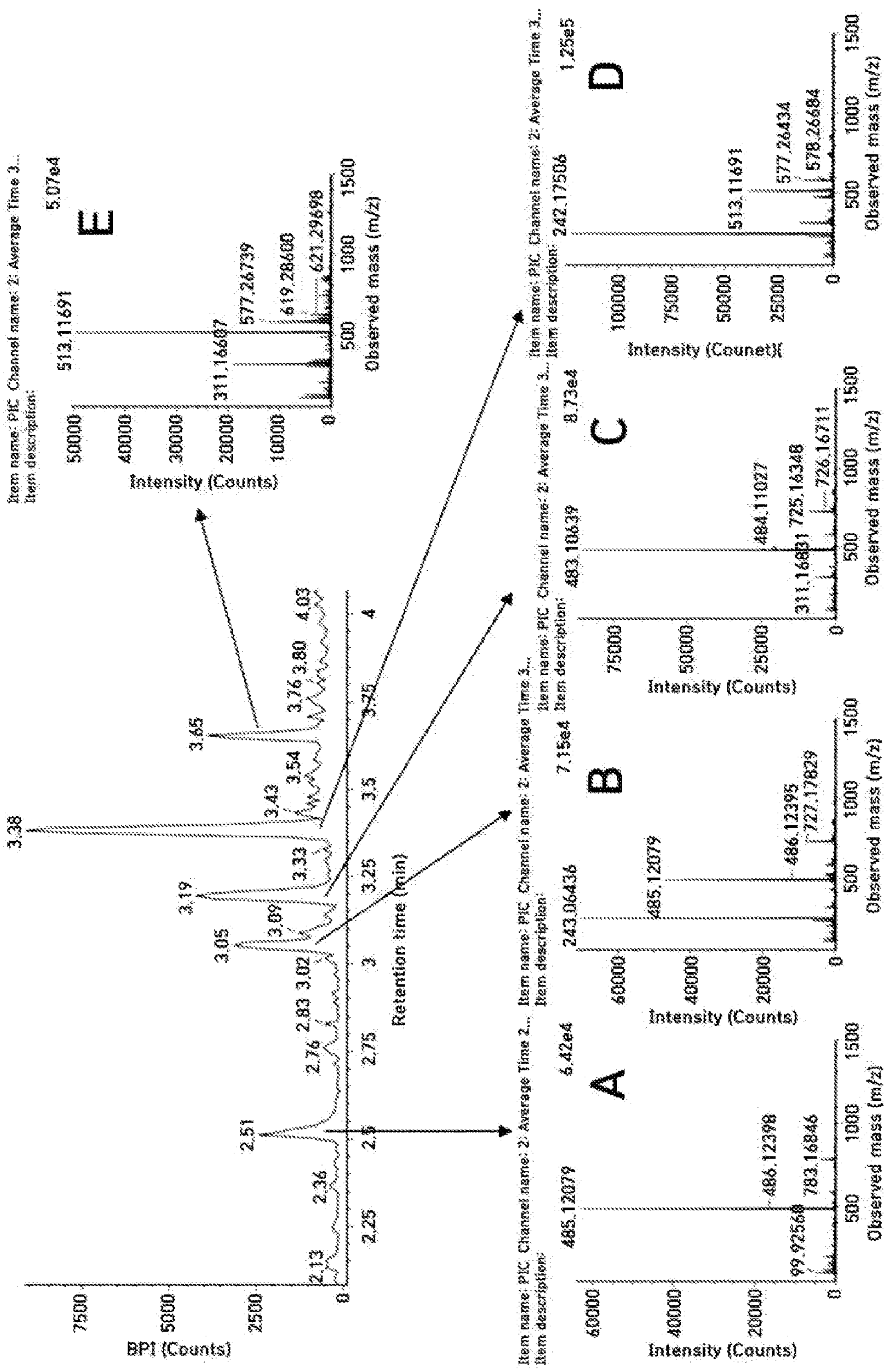
FIG. 7 illustrates the LC/MS analysis results for a product obtained by bioconversion of monomeric piceatannol using a grape callus culture solution as a plant callus culture solution according to the present invention.

<Example 8> Extraction of Piceatannol Dimer from Grape Callus Culture Solution Subjected to Bioconversion of Piceatannol and LC/MS Analysis In order to confirm the new peaks appeared in <Example 7>, the grape callus culture solution reacted in <Example 7> was subjected to water-ethyl acetate partition and extraction with the same amount of ethyl acetate. Air was injected into the obtained ethyl acetate layer for drying, and the dried product was dissolved in 100% methanol, filtered through a 0.2 μm PTFE filter (hydrophilic, ADVANTEC, Japan), and then used in LC/MS analysis. For LC/MS, UPLC-Q-TOF MS (Xevo™ G2-S, Waters, Miliford, MA, USA) and Acquity UPLC BEH C18 column (2.1 mm×100 mm, 1.7 μm; Waters) were used, and water (A) to which 0.1% FA was added and acetonitrile (B) to which 0.1% FA was added were used as the mobile phase. The mobile phase gradient conditions are presented in the following Table 1. As a result, two peaks presumed to be piceatannol dimer and one peak presumed to be piceatannol-2H-dimer were confirmed (FIG. 7).

TABLE 1

| Time | Flow Rate (ml/min) | % A | % B |
|---|---|---|---|
| initial | 0.35 | 70 | 30 |
| 1.00 | 0.35 | 70 | 30 |
| 6.00 | 0.35 | 0 | 100 |
| 7.00 | 0.35 | 0 | 100 |
| 7.20 | 0.35 | 70 | 30 |
| 9.00 | 0.35 | 70 | 30 |

<Example 9> Separation of Maackin from Grape Callus Culture Solution and NMR Analysis The ethyl acetate layer obtained by subjecting the grape callus culture solution prepared in <Example 4> to water-ethyl acetate partition and extraction was concentrated under reduced pressure. The obtained concentrate (300 mg) was subjected to the first step separation using a reverse phase column (20×500 mm) and a recycling preparative HPLC instrument. At this time, elution was performed using a water-methanol mixed solution at a ratio of 25:75 as the eluent to obtain four fractions (A to D). The fraction C containing a large amount of maackin (represented by the following Chemical Formula 1) of the target compound was concentrated to obtain 140 mg of a concentrate. The separation was performed using 140 mg of the obtained concentrate under the mixed solvent conditions as described above using a Recycling LC instrument to obtain 25 mg of maackin. The structure of the obtained compound was identified using $^{1}$H-NMR, $^{13}$C-NMR, $^{2}$D-NMR, DEPT, and mass spectrometer.

Maackin: yellow pale, 1HNMR (500 MHz, CD3OD) δ 7.118 (1H, d, ϑ=2.0 Hz), 7.050 (1H, dd, ϑ, =1.5, 8.5 Hz), 6.965 (1H, d, ϑ=15.5 Hz), 6.934 (1H, d, ϑ=8.5 Hz), 6.856 (1H, d, ϑ=16.5 Hz), 6.640 (1H, s), 6.636 (1H, d, ϑ=8.5 Hz), 6.451 (2H, s), 6.440 (1H, d, ϑ=2.5 Hz), 6.158 (2H, d, ϑ=14.0 Hz), 6.082 (1H, s), 6.078 (1H, s), 4.705 (2H, d, ϑ=2.5 Hz); 13CNMR (125 MHz, CD3OD) δ 158.3 (C-11a,13a), 157.9 (c-11b, 13b), 145.3 (C-4a), 144.7 (C-3a), 143.6 (C-3b), 139.6 (C-9a,4b), 138.7 (C-9b), 131.2 (C-1b), 128.0 (C-1a), 127.7 (C-7b), 127.0 (C-8b), 119.7 (C-6b), 119.3 (C-6a), 116.8 (C-5b), 114.6 (C-5a), 114.4 (C-2b), 114.2 (C-2a), 106.0 (C-10b, 14b), 104.5 (C-102.2 (C-12b), 101.5 (C-12a), 80.9 (C-7a), 80.504 (C-8a)

[Chem. 1]

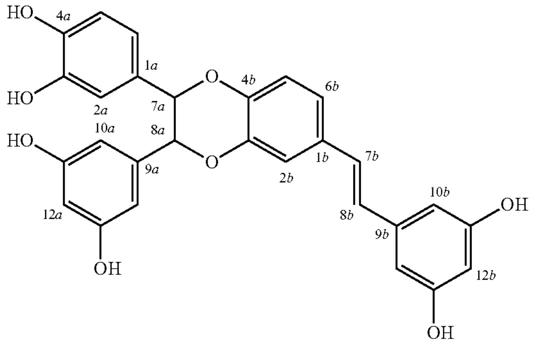

INDUSTRIAL APPLICABILITY

The method according to the present invention can be usefully used as a method for producing a dimeric stilbene. In addition, the method according to the present invention has an advantage of saving the cost and time since the use of a solubilizing agent, a peroxidase used for bioconversion, and the like can be diminished in the method.

The invention claimed is:

1. A method for producing maackin as a dimeric stilbene using a grape callus culture solution, the method consisting of:

i) suspension-culturing a grape callus in a culture medium and collecting a culture solution by separating the suspension-cultured grape callus and the culture medium; and ii) adding an extraction solvent to the culture solution collected in step i) and extracting maackin, wherein the culture medium in step i) consists of Murashige & Skoog (MS) medium and 1 mg/L of 2-4-dichlorophenoxy acetic acid (2,4-D), and wherein the culture solution in step i) is a supernatant medium separated by centrifugation of the suspension-cultured grape callus and the culture medium.

2. The method for producing maackin as a dimeric stilbene using a grape callus culture solution according to claim 1, wherein the culture solution is obtained by suspension-culturing grape callus in a culture medium for 2 to 6 days and collecting the culture solution.

3. The method for producing maackin as a dimeric stilbene using a grape callus culture solution according to claim 1, wherein the extraction solvent is ethyl acetate.

4. The method for producing maackin as a dimeric stilbene using a grape callus culture solution according to claim 1, wherein maackin is represented by the following Chemical Formula (1):

[Chem. 1]

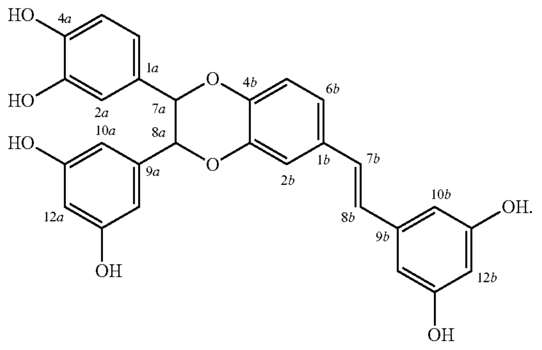

5. A composition for production of maackin as a dimeric stilbene, which comprises a grape callus culture solution as a plant callus culture solution as an active ingredient.

6. The method for producing maackin as a dimeric stilbene using a grape callus culture solution according to claim 1, wherein the suspension-cultured grape callus recovered by centrifugation is reusable for further culturing.

* * * * *